United States Patent [19]

Bender

[11] Patent Number: 5,007,417
[45] Date of Patent: Apr. 16, 1991

[54] ANKLE BRACE

[75] Inventor: Kelly M. Bender, Ashland, Wis.

[73] Assignee: Mikros U.S.A., Inc., Ashland, Wis.

[21] Appl. No.: 503,056

[22] Filed: Apr. 2, 1990

[51] Int. Cl.[5] .................. A61F 3/00; A61F 5/00; A61F 13/06

[52] U.S. Cl. ................ 128/80 H; 128/80 R; 128/165; 128/166; 36/89

[58] Field of Search .............. 128/80 H, 80 R, 166, 128/165; 36/89

[56] References Cited

U.S. PATENT DOCUMENTS

| | | | |
|---|---|---|---|
| 1,743,689 | 1/1930 | Seroggins | 36/89 |
| 2,444,428 | 7/1948 | Carrier | 36/89 X |
| 3,028,861 | 1/1960 | Shapiro | 36/89 X |
| 3,298,365 | 1/1967 | Lewis | 128/80 R |
| 3,419,974 | 1/1969 | Lange | 36/89 X |
| 4,237,874 | 12/1980 | Nelson | 128/80 H |
| 4,280,488 | 7/1981 | Polsky et al. | 128/80 H |
| 4,323,058 | 4/1982 | Detty | 128/166 X |
| 4,385,456 | 5/1983 | Livernois et al. | 36/89 X |
| 4,727,863 | 3/1988 | Nelson | 128/80 H |
| 4,878,504 | 11/1989 | Nelson | 128/80 H |

FOREIGN PATENT DOCUMENTS 728254 12/1931 France .................. 36/89

Primary Examiner—Richard J. Apley
Assistant Examiner—Linda C. M. Dvorak
Attorney, Agent, or Firm—Burd, Bartz & Gutenkauf

[57] ABSTRACT

An ankle brace for providing generalized support to the ankle has a base and a tongue assembly that is separate from the base and is connected to the base in encompassing relationship to the ankle by a lace. The base has forward lateral and medial edges that straddle the foot and ankle, each edge having a row of lace eyelets. The tongue assembly has a wrap that fits over the front and the forward side portions of the foot and ankle, and a frontal member that overlies the front superior foot portion. The frontal member has lateral and medial edges that are situated close to the lateral and medial edges of the base, each edge also having a row of lace eyelets. A single lace has a lateral segment that is alternately trained through the lateral eyelets of the frontal tongue member and the lateral edge of the base, and a medial segment that is alternately trained through eyelets on the medial edge of the frontal tongue member and the medial edge of the base. The tension force of the lace is distributed comfortably across the front superior foot portion and is not concentrated down a single line on the front of the foot.

20 Claims, 3 Drawing Sheets

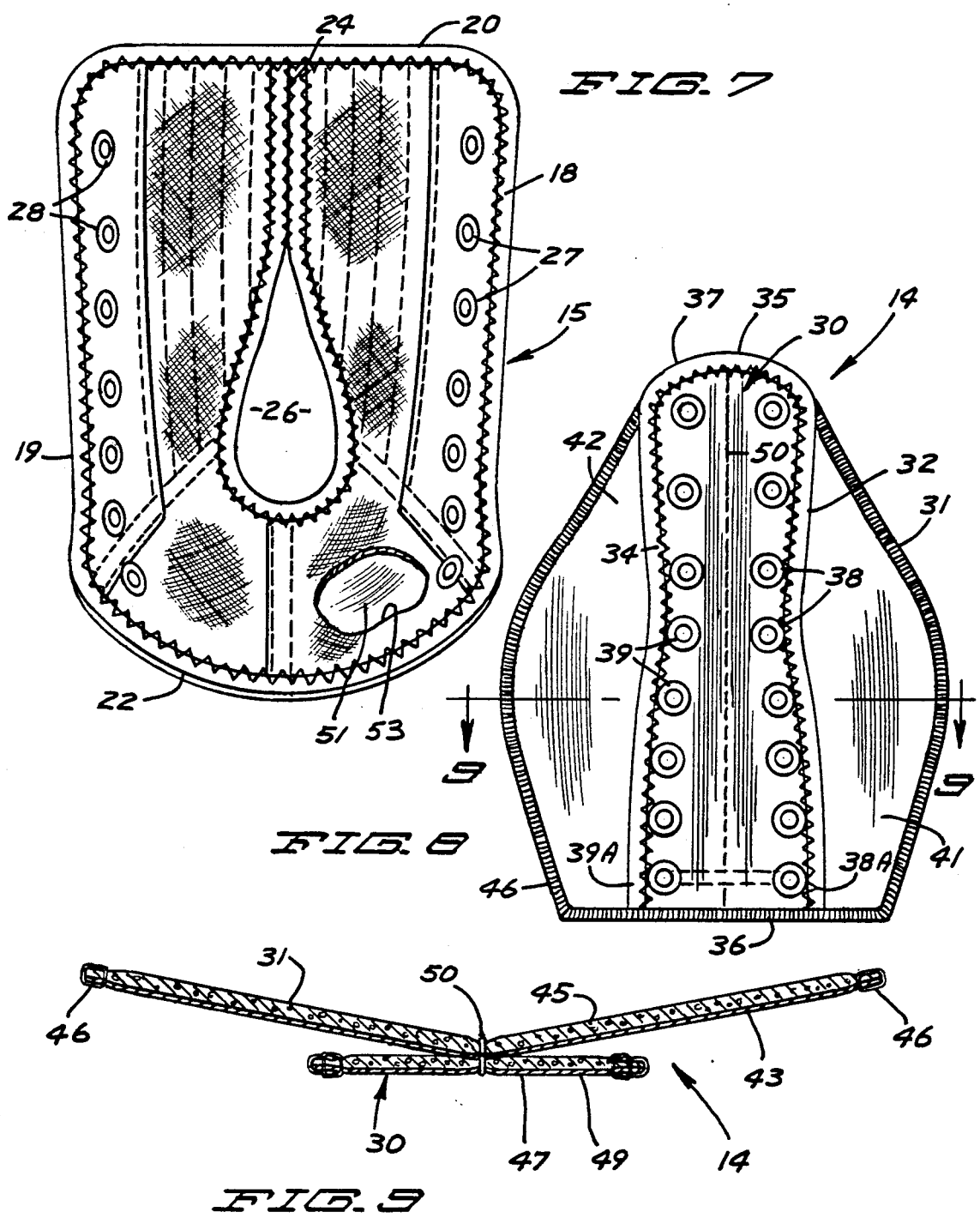

ANKLE BRACE

BACKGROUND OF THE INVENTION

The ankle joint is one of the most used joints of the body and consequently one of the most abused. It is the complex articulation point of the fibula and tibia with the ankle bone or talus and the tarsal bones. Complex ligament systems connect the various bones of the ankle joint and constrain it for movement up and down or movement in dorsiflexion and plantar flexion. The ankle is not meant to rotate from side to side or to tilt inward or outward. Traumatic movement of the ankle in such direction can result in injury or sprain to one or more of the ligament systems. For this reason athletes or other persons engaged in rigorous activity commonly use protective devices such as an elastic wrap or tape. Ankle brace devices are frequently used in favor of elastic wraps or tape. Such braces are configured to conform to the ankle region and foot, and have forward edges that come together over the front superior foot portion. The forward edges have lace eyelets and are secured on the foot by tightening a common lace trained through the lace eyelets. This concentrates a tension force down the middle of the front superior foot portion. When tightly laced, this can be uncomfortable.

SUMMARY OF THE INVENTION

The invention relates to an ankle brace that provides generalized support to the foot and ankle of a wearer engaged in rigorous activity such as an active sport. The ankle brace has a separate base and tongue assembly. the base is installed in partially surrounding relationship to the foot and ankle and has lateral and medial forward edges that straddle the foot and ankle in spaced apart relationship separated by the front superior foot portion when the base is installed on a foot and ankle. A tongue assembly is installed on the front of the foot and ankle and spans the space between the forward edges of the base. The tongue assembly includes a frontal member or tongue member having lateral and medial edges. The lateral and medial forward edges of the base and the lateral and medial edges of the tongue assembly have corresponding lace eyelets. The frontal member of the tongue assembly is connected to the forward edges of the base by a single elongate lace. A medial lace segment connects the medial edges of the frontal tongue member to the medial forward base edge, and in like fashion the lateral lace segment is trained through the eyelets on the lateral base forward edge and the lateral edge of the frontal member of the tongue assembly. The tension force of the lace is comfortably distributed across the front superior foot and ankle region rather than being concentrated along a single line on the front of the foot.

IN THE DRAWINGS

FIG. 7 is a front plan view of the base of the ankle brace of the invention in an open configuration to show the inside thereof;

FIG. 8 is a front plan view of the tongue assembly of the ankle brace of the invention in a spread open configuration; and FIG. 9 is an enlarged sectional view of a portion of the tongue assembly of FIG. 8 taken along the line 9—9 thereof.

DESCRIPTION OF A PREFERRED EMBODIMENT

Figure 1:
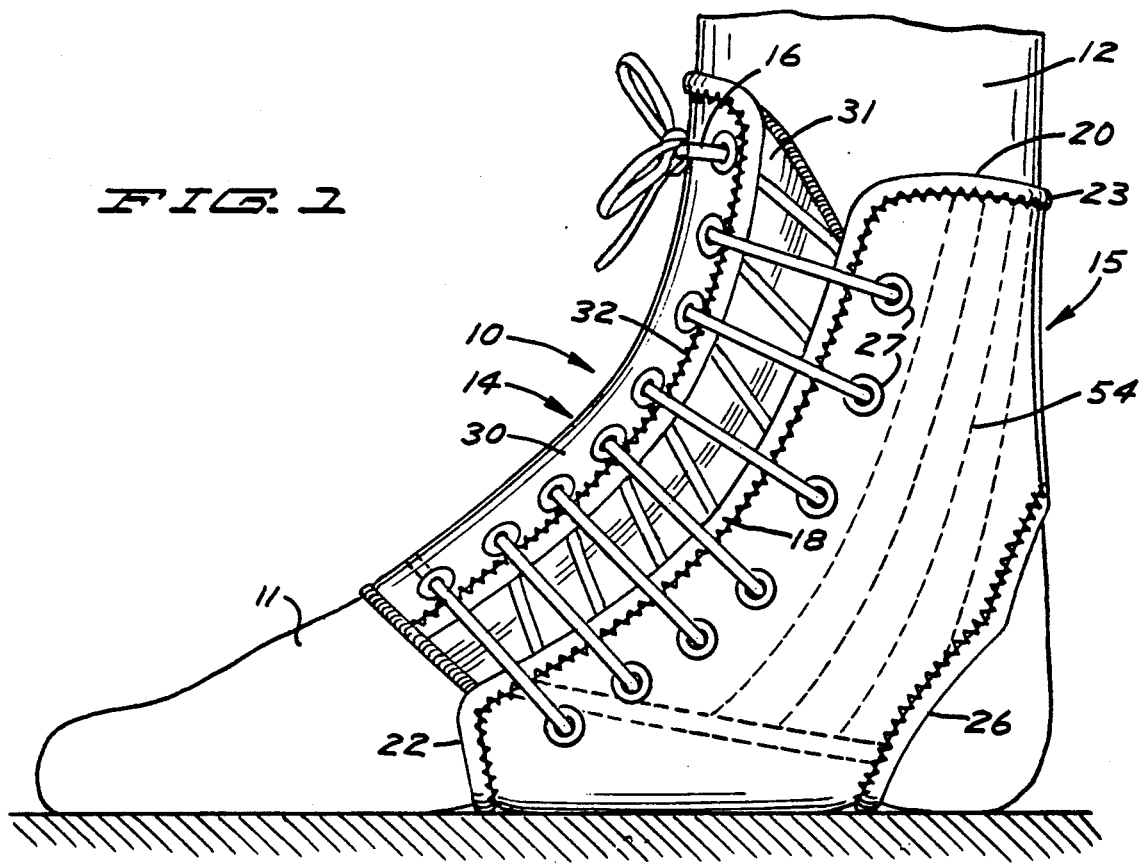
FIG. 1 is a side elevational view of an ankle brace according to the invention installed on a foot and ankle and showing the medial side thereof.

Referring to the drawings, there is shown in FIGS. 1 through 4 an ankle brace according to the invention indicated generally at 10 installed on a right foot and ankle 11 extending from the lower leg 12 to the mid-foot in covering and supportive relationship to the ankle region. Brace 10 provides generalized support to the foot and ankle 11 tending to inhibit the ankle from rotation and twisting and from flexure beyond normal limits.

Figure 5:
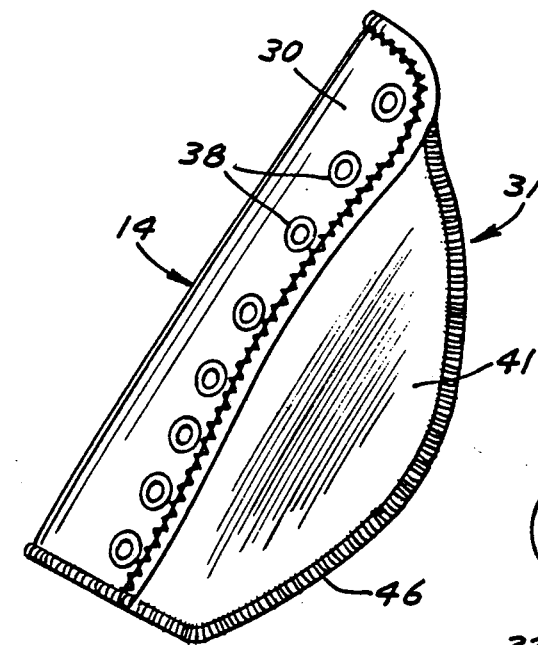
FIG. 5 is a side elevational view of the tongue assembly of the ankle brace of the invention.
Figure 6:
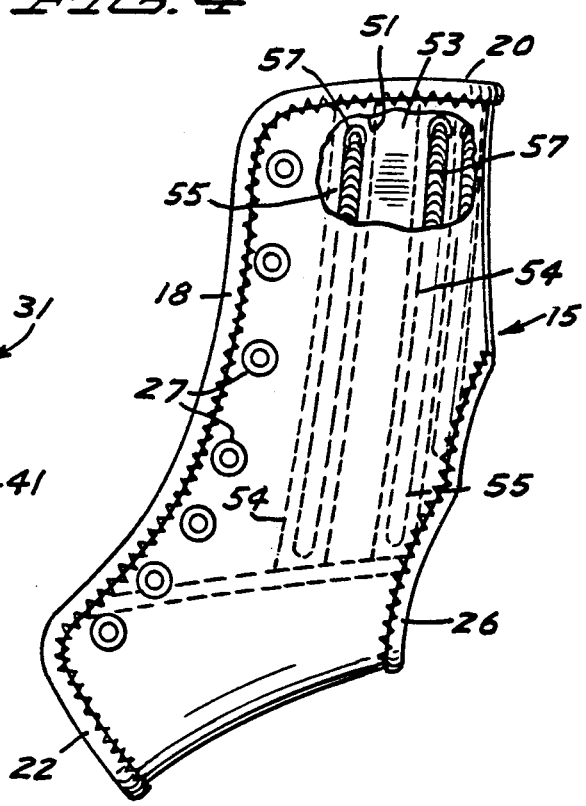
FIG. 6 is a side elevational view of the base of the ankle brace of the invention partly fragmented for purposes of illustration.

Brace 10 includes a tongue assembly 14 (FIG. 5) and a separate base 15 (FIG. 6). In installed relationship relative to foot and ankle 11, the tongue assembly 14 and base 15 are connected by a single elongate lace 16. Base 15 is formed of a flexible sheet material shaped to closely encompass the lateral and medial sides and the rearward side of foot and ankle 11 and lower leg 12. Base 10 has first and second forward edges including a medial edge 18 and a lateral edge 19. A top edge 20 is connected to the upper ends of the lateral and medial edges 18, 19 and extends around lower leg 12 in partially surrounding relationship. A front edge 22 is connected to the lower ends of the medial and lateral edges 18, 19 and extends beneath the mid-foot in partially surrounding relationship. An edge binding 23 is secured to the various edges. Portions of base 15 come together at a rear seam 24 which extends adjacent the Achilles tendon. A heel opening 26 is located beneath the rear seam 24 for accommodation of the heel of the foot 11.

Base 15 installed on a foot and ankle extends only partially around the foot and ankle covering the rear and side portions thereof. The forward edges 18, 19 straddle the foot and ankle and are positioned in spaced apart relationship on medial and lateral sides of the front superior foot surface and corresponding ankle region. A row of medial eyelets 27 extends parallel to and closely adjacent the medial edge 18 on base 15. A row of lateral eyelets 28 extends parallel to and closely adjacent the lateral forward edge 19.

Tongue assembly 14 is configured to occupy the space between the medial and lateral forward edges 18, 19 of base 15 in covering relationship to the front superior foot portion and the corresponding ankle portion of foot and ankle 11. Tongue assembly 14 has a length generally corresponding to the forward edges 18, 19 and includes a tongue member or frontal member 30 and a foot cover or wrap 31. Frontal member 30 is an elongate narrow member having a first or medial edge 32 and a second or lateral edge 34, a top edge 35 and a bottom edge 36, and can be centrally narrowed between the side edges as shown in FIG. 8 for purposes of better conforming to the front superior surface of the foot. An edge binding 37 covers the various edges of the frontal member 30.

Frontal member 30 has a first row of medial eyelets 38 extending parallel to and closely adjacent to the medial edge 32, positionable generally in alignment for connection to the medial eyelets 22 on the medial edge 18 of base 15. A second row of lateral eyelets 39 extends parallel to and closely adjacent the lateral edge 34 of frontal member 30, positionable in alignment for connection to the lateral eyelets 28 along the lateral forward edge 19 of base 15.

As shown in FIGS. 8 and 9, wrap 31 includes a medial panel 41 and a lateral panel 42 configured to extend around the medial and lateral sides of the foot in underlying relationship to the medial and lateral edges 18, 19 of base 15. Wrap 31 is formed of an outward facing or outer layer 43 of flexible, sheet-like material such as vinyl and an inner liner 45 of soft material such as a foam material secured to the outer layer 43 by edge stitching 46. Frontal member 30 is also comprised of an outer layer 47 and a liner 49 that is inwardly facing and of a soft material such as a fabric backed foam material. Frontal member 30 is connected to wrap 31 by a central seam 50 extending almost the length thereof, and by the edge stitching 46 of wrap 31 along the lower edge 36 of frontal member 30. Seam 50 is interrupted or terminated at the expanse between the lower most medial and lateral eyelets 38A, 39A of frontal member 30 for the purpose of training the central portion of lace 16 between them.

Base 15 is formed of an outer layer 51 of a sheet-like flexible material such a vinyl, and an inner layer 53 of a soft material such as a fabric backed foam. The outer and inner layers 51, 53 are joined by edge binding 23. A plurality of upright or vertical seams 54 on the lateral and medial sides of base 15 are formed between the inner and outer layers 51, 53. The seams 54 form a plurality of upright pockets 55. Pockets 55 extend from a location on the lower medial and lateral sides of base 15 to approximately the upper edge 20. A plurality of elongate stay members 57 are positioned in select pockets 55. Stay members 57 are resilient and provide additional support to the ankle region when base 15 is installed upon the foot and ankle. Stay members 57 can be the type constructed of a pair of interleaved and flattened helical springs.

Figure 2:
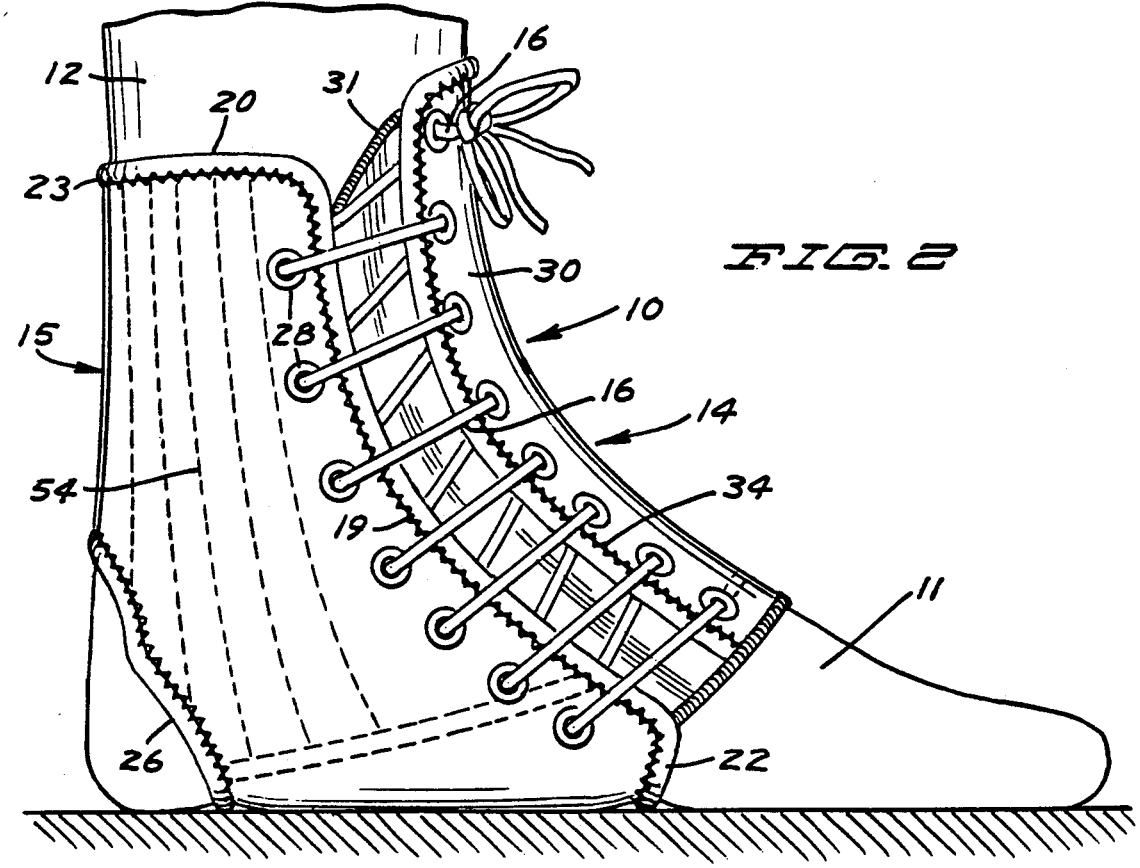
FIG. 2 is a side elevational view of the ankle brace installed on the foot and ankle of FIG. 1 showing the lateral side thereof.
Figure 3:
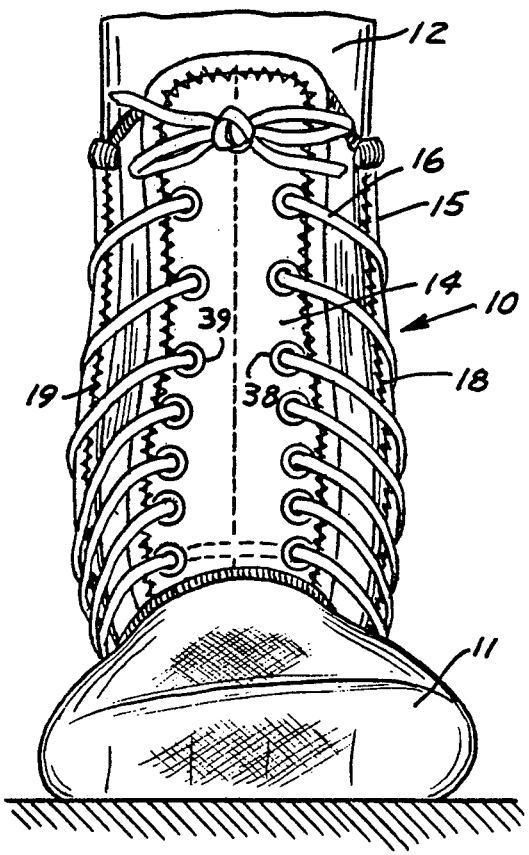
FIG. 3 is a front elevational view of the ankle brace installed on the foot and ankle of FIG. 1.
Figure 4:
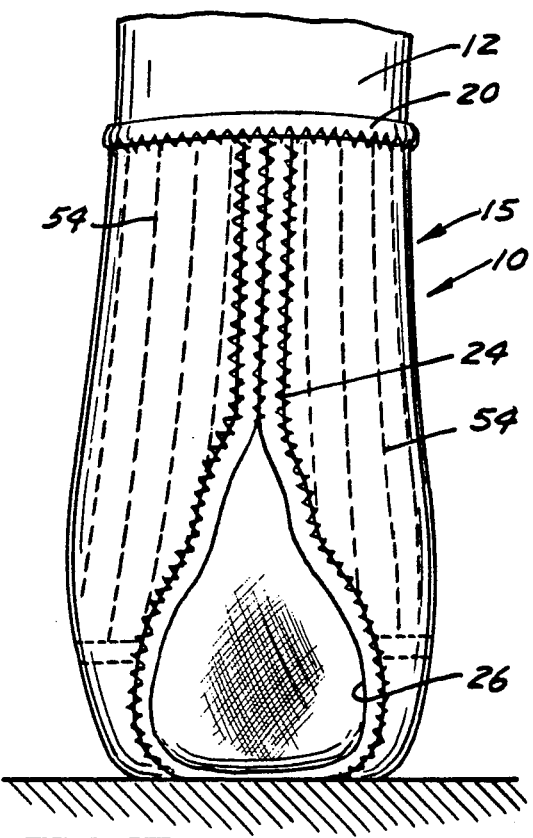
FIG. 4 is a rear elevational view of the ankle brace installed on the foot and ankle of FIG. 1.

In the use of ankle brace 10, the tongue assembly 14 is initially loosely assembled to base 15 by lace 16. Lace 16 is trained through the lower eyelets 38A, 39A on tongue assembly 14 so that the central portion thereof is located in the space between the eyelets with a medial lace segment extending from the medial eyelet 38A and a lateral lace segment extending from the lateral eyelet 39A. The medial segment is trained alternately through the medial eyelets 27 on base 15 and the medial eyelets 38 on the frontal member 30 of tongue assembly 14. Likewise, the lateral lace segment is trained alternately through the lateral eyelets 28 on base 15 and the lateral eyelets 39 on the frontal member 30. With the tongue assembly loosely assembled to the base 15, the foot is inserted between them. The heel is placed in heel opening 26 and the lateral and medial panels 41, 42 of the wrap 31 are positioned over lateral and medial sides of the foot with the frontal member 30 spanning the front superior foot portion. In such relationship, the lace 16 is tightened with respect to the various eyelets and then tied with a common bow knot as shown in FIGS. 1 through 3. The base and tongue assembly can be drawn in tightly about the foot to provide for good support. The force of the lace being tightened is distributed accross the medial and lateral sides of the foot as well as the front superior foot portion. There is no single concentration of force down the central portion of the foot. This results in greater comfort to the wearer.

While there has been shown and described a certain preferred embodiment of the invention, it will be apparent that certain deviations can be had without departing from the scope and spirit of the claims.

The embodiments of the invention in which an exclusive property or privilege is claimed are defined as follows:

1. An ankle brace comprising:
   a flexible base configured to fit around the rearward and side portions of the foot and ankle having medial and lateral forward edges positionable in straddling spaced apart relationship to the foot and ankle on medial and lateral sides thereof;
   tongue means separate from the base configured to cover the front superior ankle and foot portions between the lateral and medial forward edges of the base, said tongue means having a tongue member narrower than the distance between the forward edges of the base when positioned on a foot and a first edge positionable in parellel spaced side-by-side relationship to the medial edge of the base, and a second edge positionable in parallel spaced side-by-side relationship to the lateral edge of the base when the base and tongue means are installed on a foot;
   first lace fastening means including lace eyelets and a lace cooperating between the first edge of the tongue member and the medial edge of the base to fasten them together, and second lace fastening means including lace eyelets and a lace cooperating between the second edge of the tongue means and the lateral edge of the base to fasten them together and secure the tongue member and the base in encompassing relationship to a foot and ankle.

2. The ankle brace of claim 1 wherein: said first and second fastening means include lace means.

3. An ankle brace comprising:
   a flexible base configured to fit around the rearward and side portions of the foot and ankle having medial lateral forward edges positionable in straddling relationship to the foot and ankle on medial and lateral sides thereof;
   tongue means separate from the base configured to cover the front superior ankle and foot portions between the lateral and medial forward edges of the base, said tongue means having a first edge positionable in parallel juxtaposed relationship to the medial edge of the base, and a second edge positionable in parallel juxtaposed relationship to the lateral edge of the base when the base and tongue means are installed on a foot;
   said tongue means including an elongate tongue member having said first and second edges, and a wrap secured to the tongue member and covering the front superior foot and ankle region in underlying relationship relative to the forward edges of the base;
   first fastening means cooperating between the first edge of the tongue means and the medial edge of the base to fasten them together, and second fastening means cooperating between the second edge of the tongue means and the lateral edge of the base to fasten them together and secure the tongue means and the base in encompassing relationship to a foot and ankle.

4. The ankle brace of claim 3 wherein: said lace means includes a single elongate lace.

5. The ankle brace of claim 4 including: a heel opening on the base positioned for accomodation of the heel of a foot.

6. An ankle brace comprising:

a flexible base configured to fit around the rearward and side portions of the foot and ankle having medial and lateral forward edges positionable in straddling relationship to the foot and ankle on medial and lateral sides thereof;

tongue means separate from the base configured to cover the front superior ankle and foot portions between the lateral and medial forward edges of the base, said tongue means having a first edge positionable in parallel juxtaposed relationship to the medial edge of the base, and a second edge positionable in parallel juxtaposed relationship to the lateral edge of the base when the base and tongue means are installed on a foot;

first fastening means cooperating between the first edge of the tongue means and the medial edge of the base to fasten them together, and second fastening means cooperating between the second edge of the tongue mens and the latral edge of the base to fasten them together and secure the tongue means and the base in encompassing relationship to a foot and ankle;

said fastening means including a row of medial eyelets on the base parallel to and closely adjacent to the medial edge, a row of lateral eyelets on the base parallel to and closely adjacent the lateral eyelets on the base parallel to and closely adjacent the lateral edge, a first row of eyelets on the tongue means parallel to and closely adjacent the first edge, a second row of eyelets on the tongue means parallel to and closely adjacent the second edge, and lace means interconnecting the first row of eyelets and the medial eyelets, and interconnecting the second row of eyelets and the lateral eyelets to fasten the tongue means to the base means in encompassing relationship to an ankle and foot.

7. The ankle brace of claim 6 wherein: said lace means includes a single elongate lace, said tongue means includes an elongate tongue member having said first and second edges, and a wrap secured to the tongue member and covering the front superior foot and ankle region in underlying relationship relative to the forward edges of the base.

8. An ankle brace for encompassing the ankle and mid-foot in supportive relation thereto, comprising:

a base of flexible sheet material shaped to encompass the rearward and side portions of the ankle and adjacent foot portion in partially surrounding relationship, said base having medial and lateral forward edges positioned in straddling relationship to the foot and ankle when the base is installed upon a foot, a medial row of lace eyelets parallel to and closely adjacent the medial forward edge of the base, a lateral row of lace eyelets parallel to and closely adjacent the lateral edge of the base;

a tongue assembly separate from the base including a tongue member having first and second edges and a length generally corresponding to the length of the forward edges of the base and positionable in covering relationship to the front superior foot and ankle region between the forward edges of the base with the first edge located adjacent the medial edge of the base and the second edge located adjacent the lateral edge of the base, a first row of lace eyelets on the tongue member parallel to and closely adjacent the first edge, a second row of lace eyelets on the tongue member parallel to and closely adjacent the second edge, and lace means connecting the first row of eyelets and the medial row of eyelets on the medial edge of the base and connecting the second row of eyelets and the lateral row of eyelets on the lateral edge of the base.

9. The ankle brace of claim 8 including: said tongue assembly includes a wrap connected to the tongue member and configured to cover the front superior foot and ankle region.

10. The ankle brace of claim 9 wherein: said wrap includes a medial panel positioned in underlying relationship to the medial edge of the base, and a lateral panel positioned in underlying relationship to the lateral edge of the base when the base and tongue assembly are installed on a foot and ankle.

11. The ankle brace of claim 10 wherein: said lace means includes a single elongate lace having a medial part trained alternately through eyelets of the first row or eyelets and the medial row of eyelets on the base, and a lateral part trained alternately through lace eyelets of the second row of eyelets and the lateral row of eyelets on the base.

12. The ankle brace of claim 11 including: a heel opening on the base positioned for accommodation of the heel of a foot.

13. The ankle brace of claim 11 including: at least one longitudinal medial pocket on the medial side of the base, an elongate stay member located in the medial pocket, at least one longitudinal lateral pocket on the lateral side of the base, and a stay member located in the lateral pocket.

14. The ankle brace of claim 11 including: a plurality of longitudinal medial pockets on the medial side of the base, a plurality of medial stay members located in the medial pockets, a plurality of lateral pockets of the lateral side of the base, a plurality of lateral stay members located in the lateral pockets.

15. The ankle brace of claim 14 wherein: said base includes an outer layer of flexible sheet-like material and a liner connected to outer layer, said longitudinal pockets being formed by a plurality of longitudinal seams formed between the outer layer and the liner.

16. The ankle brace of claim 11 including: a central seam fixing the tongue member to the wrap.

17. The ankle brace of claim 8 wherein: said base has a top edge connected to the upper ends of the forward edges and configured to partially wrap around the lower leg, and a front edge connected to the lower ends of the forward edges in configured to partially wrap around the mid-foot.

18. The ankle brace of claim 17 wherein: said lace means includes a single elongate lace having a medial part trained alternately through eyelets of the first row of eyelets and the medial row of eyelets on the base, and a lateral part trained alternately through lace eyelets of the second row of eyelets and the lateral row of eyelets on the base.

19. The ankle brace of claim 18 including: said tongue assembly includes a wrap connected to the tongue member and configured to cover the front superior foot and ankle region.

20. The ankle brace of claim 19 wherein: said wrap includes a medial panel positioned in underlying relationship to the medial edge of the base, and a lateral panel positioned in underlying relationship to the lateral edge of the base when the base and tongue assembly are installed on a foot and ankle.

* * * * *